(12) United States Patent
Skibo et al.

(10) Patent No.: US 6,846,840 B2
(45) Date of Patent: Jan. 25, 2005

(54) CYTOTOXIC N-UNSUBSTITUTED INDOLES AND CYCLOPENT(B)INDOLES AND METHOD OF MAKING AND USING SAME

(75) Inventors: Edward B. Skibo, Mesa, AZ (US); Chengguo Xing, Somerville, MA (US)

(73) Assignee: Arizona Board of Regents acting for and on behalf of Arizona State University, Tempe, AZ (US)

( * ) Notice: Subject to any disclaimer, the term of this patent is extended or adjusted under 35 U.S.C. 154(b) by 0 days.

(21) Appl. No.: 10/173,343

(22) Filed: Jun. 17, 2002

(65) Prior Publication Data

US 2004/0006054 A1 Jan. 8, 2004

Related U.S. Application Data

(63) Continuation of application No. PCT/US00/34247, filed on Dec. 15, 2000.
(60) Provisional application No. 60/171,253, filed on Dec. 16, 1999.

(51) Int. Cl.[7] .................... C07D 209/04; C07D 403/02; A61K 31/404
(52) U.S. Cl. ....................... 514/411; 548/448; 548/962
(58) Field of Search ................................ 548/448, 962; 514/411

(56) References Cited

U.S. PATENT DOCUMENTS 5,192,789 A * 3/1993 Ong et al. .................. 514/411

* cited by examiner

Primary Examiner—Joseph K. McKane
Assistant Examiner—Golam M M Shameem

(57) ABSTRACT

The merits of N-unsubstituted indoles and cyclopent[b]indoles as DNA-directed reductive alkylating agents are described. These systems represent a significant departure from N-substituted and pyrrolo[1,2-$\alpha$] fused systems such as the mitomycins and mitosenes. The cyclopent[b]indole-based aziridinylquinone, when bearing an acetate leaving group, was found to be cytotoxic and displayed significant in vivo activity against syngeneic tumor implants. This particular analogue was unexpectedly superior to the others studied, both in terms of high specificity for the activating enzyme DT-diaphorase and in high % DNA alkylation. Alkylation by a quinone methide intermediate as well as by the aziridinyl group were examined for crosslinking. The possible metabolites of the most active indole species were prepared and found to retain cytotoxicity, strongly suggesting that in vivo activity could also be sustained. The indole systems in the present invention display selectivity for melanoma and for non small cell lung, colon, renal, and prostate cancers when administered in an effective amount. The cancer specificity observed is believed to pertain to differential substrate specificity for DT-diaphorase.

9 Claims, 1 Drawing Sheet

CYTOTOXIC N-UNSUBSTITUTED INDOLES AND CYCLOPENT(B)INDOLES AND METHOD OF MAKING AND USING SAME

This Application is based on U.S. Provisional Application Ser. No. 60/171,253 filed Dec. 16, 1999 which is a continuation of PCT Ser. No. PCT/US00/34247 on International Filing Date Dec. 15, 2000.

Financial assistance for this project was provided by the U.S. Government through the National Science Foundation under Grant Number CHE-9522640 and through the National Institutes of Health under Grant Number CA 73758; and the United States Government may own certain rights to this invention.

TECHNICAL FIELD

A new class of reductive alkylating agents possessing both in vitro cytotoxicity and antitumor activity have been discovered. Many of the compounds display a specificity toward some histological cancer types.

BACKGROUND ART

Previous findings of the lead inventor showed that small molecule reductive alkylating agents called pyrrolobenzimidazoles or PBIs (Chart 1) show a high degree of specific cytotoxicity for some cancers. {Skibo, E. B. Pyrrolobenzimidazoles in cancer treatment. *Expert. Opin. Ther. Patents.* 1998, 8, 673–701} This specificity is very likely due to the presence of the two-electron reducing enzyme DT-diaphorase, which reduces the PBI in these cells. {Zhou, R.; Skibo, E. B. Chemistry of the Pyrrolo[1,2-α]benzimidazole Antitumor Agents: Influence of the 7-Substituent on the Ability to Alkylate DNA and Inhibit Topoisomerase II. *J.Med.Chem.* 1996, 39, 4321–4331} {Skibo, E. S.; Gordon, S.; Bess, L.; Boruah, R.; Heileman, J. Studies of Pyrrolo[1,2-α]benzimidazole Quinone DT-Diaphorase Substrate Activity, Topoisomerase II Inhibition Activity, and DNA Reductive Alkylation. *J. Med. Chem.* 1997, 40, 1327–1339} Reduction of the PBI to the corresponding hydroquinone causes the aziridine nitrogen to become more basic resulting in protonation and nucleophilic attack (alkylation). Similarly, indoloquinones such as mitomycin C {Spanswick, V. J.; Cummings, J.; Smyth, J. F. Current issues in the enzymology of mitomycin C metabolic activation. *Gen.Pharmacol.* 1998, 31, 539–544} and EO9, {Bailey, S. M.; Lewis, A. D.; Knox, R. J.; Patterson, L. H.; Fisher, G. R.; Workman, P. Reduction of the indoloquinone anticancer drug EO9 by purified DT-diaphorase: A detailed kinetic study and analysis of metabolites. *Biochem.Pharmacol.* 1998, 56, 613–621} (Chart 1) require two—electron reductive activation by DT-diaphorase.

CHART 1

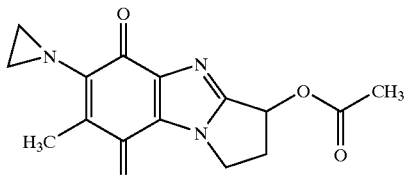

PBI-A

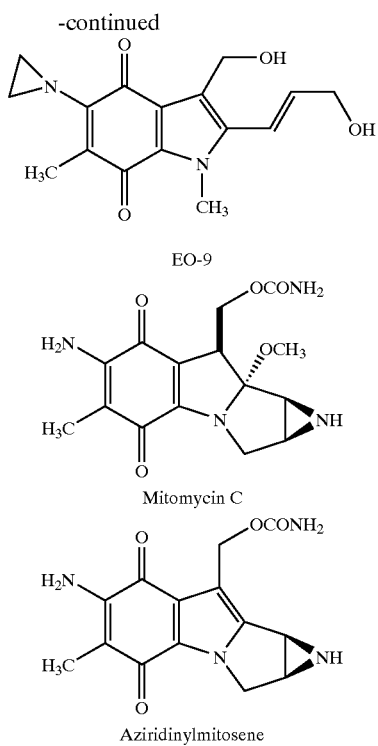

EO-9

Mitomycin C

Aziridinylmitosene

BRIEF DESCRIPTION OF THE INVENTION

The present invention relates to the design of selective cytotoxic agents based on the aziridinyl indoloquinones shown in Chart 2 below. Although indoloquinone-based antitumor agents are well known, the compounds in Chart 2 possess one distinguishing feature: an N-unsubstituted indole system. Typically, the indoloquinone-based antitumor agents (mitomycins and mitosenes) have an alkyl substituent at this position.

CHART 2

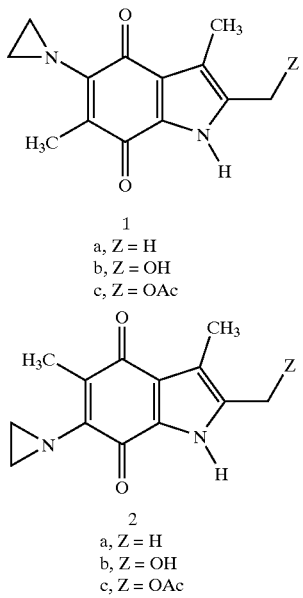

1
a, Z = H
b, Z = OH
c, Z = OAc 2
a, Z = H
b, Z = OH
c, Z = OAc

-continued

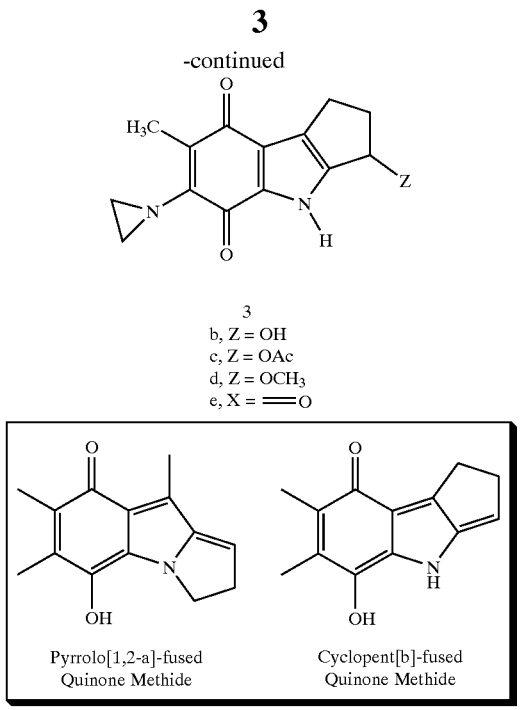

3
b, Z = OH
c, Z = OAc
d, Z = OCH₃
e, X = =O

Pyrrolo[1,2-a]-fused Quinone Methide

Cyclopent[b]-fused Quinone Methide

A possible hydrogen bond donor role in the DNA major groove for the indole NH moiety was investigated. Previously, the DNA major groove hydrogen bonding interactions with N-protonated reduced PBI antitumor agents was reported. {Schulz, W. G.; Nieman, R. A.; Skibo, E. B. Evidence for DNA Phosphate Backbone Alkylation and Cleavage by Pyrrolo[1,2α] benzimidazoles, Small Molecules Capable of Causing Sequence Specific Phosphodiester Bond Hydrolysis. *Proc. Natl. Acad. Sci. U.S.A.* 1995, 92, 11854–11858} However, the quinone methide species derived from the pyrrolo[1,2-α]—fused and the cyclopent [b]—fused systems, shown in the inset of Chart 2, were expected to possess different stability and reactivity patterns. Finally, the differential DT-diaphorase substrate specificity of these novel indole analogues could lead to cancer specificity. One cyclopent[b]indole system, 3c, possessed high in vivo activity and high cancer specificity making it a suitable compound for further development.

DESCRIPTION OF THE PREFERRED EMBODIMENT

Figure 1:
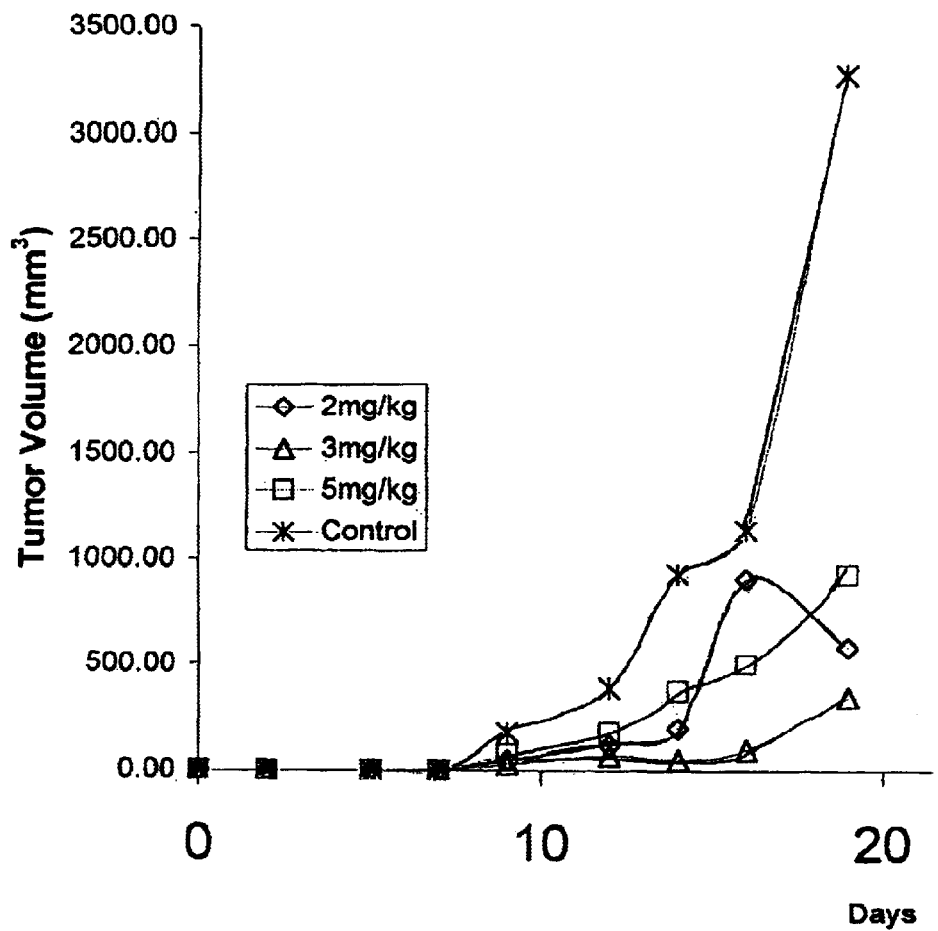
FIG. 1. Results of cyclopent[b]indole 14 in the B-16 melanoma model in C57/b1 mice (run at University of Arizona Cancer Center). This compound was studied at three dose levels: 2, 3 and 5 mg/Kg IP on days 1, 5, and 9 after tumor implantation into the front flank muscle. Shown in the plot are the AUC values as a function of time for each dosage. The control was obtained with drug-free animals.

Synthesis. The preparation of the indole series 1, which is a substituted 5-aziridinylindole-4,7-dione, was carried out as described in Scheme 1. The nitration and reduction of the previously prepared indole 4 {Boruah, R. C.; Skibo, E. B. A Comparison of the Cytotoxic and Physical Properties of Aziridinyl Quinone Derivatives Based on the Pyrrolo [1,2-α]benzimidazole and Pyrrolo[1,2-α]indole Ring Systems. *J. Med. Chem.* 1994, 37, 1625–1631} afforded indole 5, which was converted to quinone derivatives by reduction/Fremy oxidation. {Skibo, E. B.; Islam, I.; Schulz, W. G.; Zhou, R.; Bess, L.; Boruah, R. The Organic Chemistry of the Pyrrolo [1,2-α]benzimidazole Antitumor Agents. An Example of Rational Drug Design. *Synlett* 1996, 297–309} {Zimmer, H.; Lankin, D. C.; Horgan, S. W. Oxidations with Potassium Nitrosodisulfonate (Fremy's Radical). The Teuber Reaction. *Chem. Rev.* 1971, 71, 229–246}

The indole series 2, which is a substituted 6-aziridinylindole-4,7-dione, were prepared from indole 7 as outlined in Scheme 2. Access to indole 7 was achieved employing the Japp-Klingmann/Fischer Indole reactions starting with p-toluidine. This procedure is analogous to a reported indole synthesis starting with p-anisidine. {Liu, R.; Zhang, P.; T. Gan, T.; Cook, J. M. Regiospecific Bromination of 3-Methylindoles with NBS and Its Application to the Concise Synthesis of Optically Active Unusual Tryptophans Present in Marine Cyclic Peptides. *J Org Chem* 1997, 62, 7447–7456}

SCHEME 1

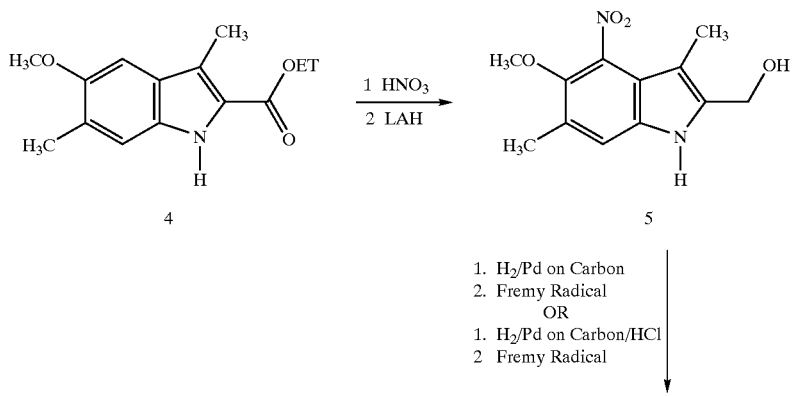

1. H₂/Pd on Carbon
2. Fremy Radical
   OR
1. H₂/Pd on Carbon/HCl
2. Fremy Radical

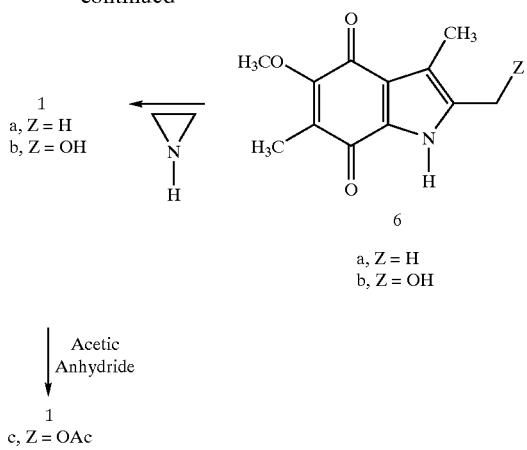

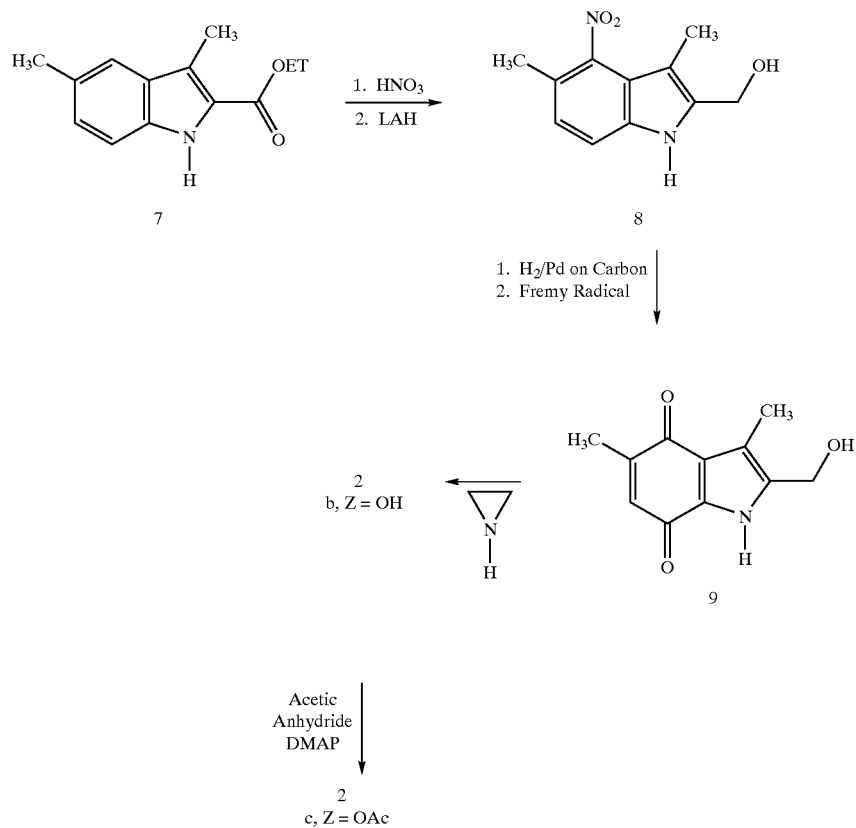

The preparation of the cyclopentane-fused indole series 3, which is a substituted 6-Aziridinyl-1,4-Dihydro-3-hydroxy-(2H) cyclopent[b]indole-5,8-dione, was carried out as outlined in Scheme 3 starting with cyclopent[b]indole 10. The preparation of cyclopent[b]indole 10 was accomplished by employing the Fischer Indole reaction starting with 1,2-cyclopentanedione {Acheson, R. M. Some Experiments with Cyclopentanes. *J.Chem.Soc.* 1956, 4232–4237} and p-tolylhydrazine. The nitration of cyclopent[b]indole 10 afforded only the 8-nitro derivative, identifiable by an AB quartet in the aromatic region with a J value=8.7 Hz. The carbonyl and nitro groups were reduced by borohydride and $H_2$/Pd on Carbon, respectively, followed by Fremy oxidation to afford cyclopent[b]indoles 12 and 13. The formation of compound 12 was achieved by a three-step process: namely, the elimination of water from 11 resulting in a quinone methide, the addition of methanol solvent to this species, and finally the Fremy oxidation to the quinone product. Cyclopent[b]indole 12 was converted to cyclopent[b]indole 3d. The alcohol derivative cyclopent[b]indole 3b was converted to cyclopent[b]indoles 3c, 3e, and 14.

SCHEME 3

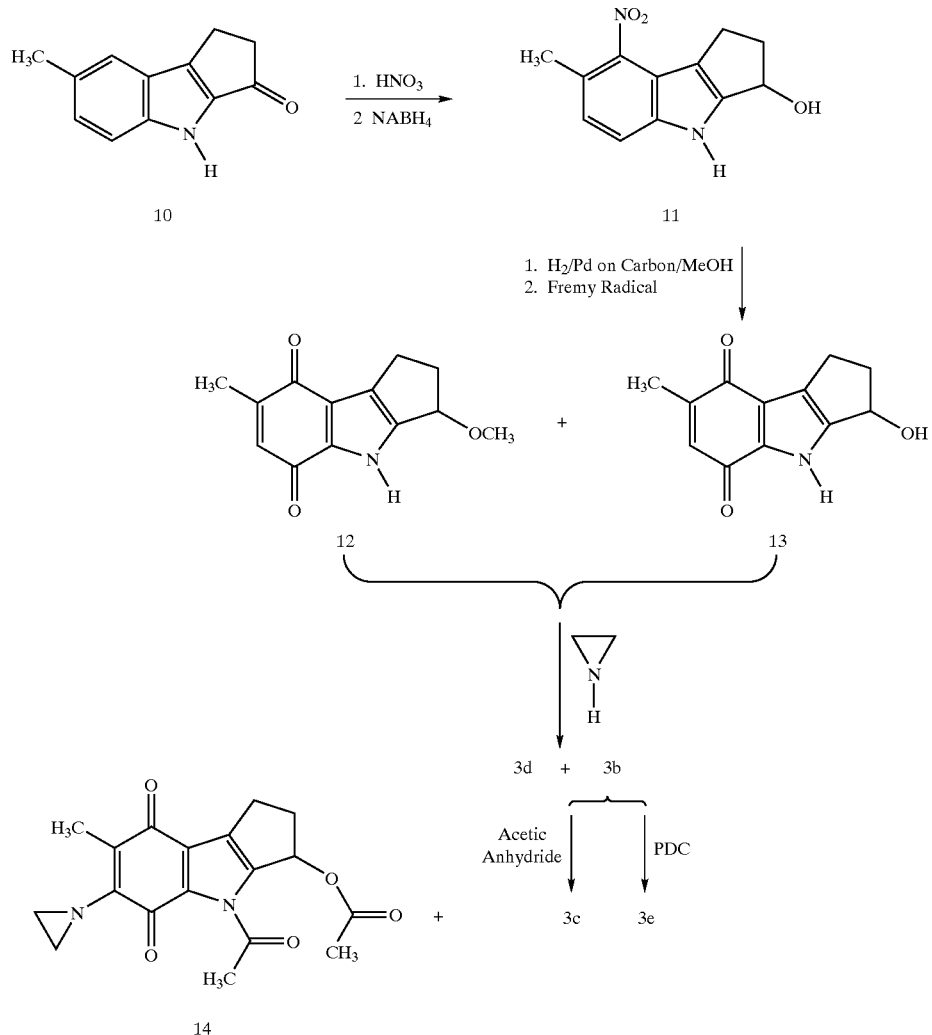

In Vitro Screening Results. The cytotoxicity of the indole series 1–2 and cyclopent[b]indole 3 against a variety of cancer cell lines are shown in Tables 1–3. These data were derived from National Cancer Institute mean graph data and are not direct reproductions thereof. For each histologic cancer type, the average $-\log LC_{50}$ value was determined from an NCI panel consisting of six to eight human cancer cell lines. {Paull, D. K.; Shoemaker, R. H.; Hodes, L.; Monks, A.; Scudiero, D. A.; Rubinstein, L.; Plowman, J.; Boyd, M. R. Display and Analysis of Differential Activity of Drugs Against Human Tumor Cell Lines: Development of Mean Graph and COMPARE Algorithm. *J.Natl.Cancer Inst.* 1989, 81, 1088–1092} {Alvarez, M.; Robey, R.; Sandor, V.; Nishiyama, K.; Matsumoto, Y.; Paull, K.; Bates, S.; Fojo, T. Using the national cancer institute anticancer drug screen to assess the effect of mrp expression on drug sensitivity profiles. *Mol.Pharmacol.* 1998, 54, 802–814}

Comparison of Tables 1 and 2 reveals the importance of the position of the aziridinyl group: when this group was moved from the 5- to the 6-position, cytotoxic activity was substantially decreased. The importance of the position of the aziridinyl ring in cytotoxicity was also apparent in the PBIs. {Skibo, E. B.; Islam, I.; Heileman, M. J.; Schulz, W. G. Structure-Activity Studies of Benzimidazole—Based DNA—Cleaving Agents. Comparison of Benzimidazole, Pyrrolobenzimidazole and Tetrahydropyridobenzimidazole Analogues. *J.Med.Chem.* 1994, 37, 78–92}

TABLE 1

Table of Log $LC_{50}$ (where $LC_{50}$ is the concentration in moles/liter causing 50% lethality) values (columns) and histological cancer type (rows) for the indole series 1a–c. Each cancer type represents the arithmetic average of six to eight different cancer cell lines. Melanomas are the most sensitive cancer to this series of indoles, followed by prostate and colon for the more active indole analogues 1b and 1c.

| CANCER | Indole, 1a | Indole, 1b | Indole, 1c |
|---|---|---|---|
| LEUKEMIA | >−4 | >−4 | >−4 |
| NSC LUNG | −4.29 | −4.37 | −4.48 |
| COLON | >−4 | −4.32 | −5.08 |
| CNS | >−4 | >−4 | −4.83 |
| MELANOMA | −4.42 | −5.39 | −5.64 |
| OVARIAN | >−4 | >−4 | −4.46 |
| RENAL | >−4 | −4.53 | −4.54 |
| PROSTATE | >−4 | −4.78 | −5.01 |
| BREAST | >−4 | −4.56 | −4.57 |

TABLE 2

Table of Log $LC_{50}$ (where $LC_{50}$ is the concentration in moles/liter causing 50% lethality) values (columns) and histological cancer type (rows) for the indole series 2a–c. Each cancer type represents the arithmetic average of six to eight different cancer cell lines. The large log $LC_{50}$ values in the acetate substituted indoles 2c and to a lesser extent 2b, compared to 1c and 1b respectively in Table 1, reflect the substantial loss of cytotoxicity observed when the aziridinyl group is moved from the 5- to the 6- position.

| CANCER | Indole 2a | Indole 2b | Indole 2c |
|---|---|---|---|
| LEUKEMIA | >−4 | >−4 | >−4 |
| NSC LUNG | −4.3 | −4.1 | −4.1 |
| COLON | −4.05 | −4.2 | >−4 |
| CNS | >−4 | −4.05 | >−4 |
| MELANOMA | −4.15 | −4.4 | −4.15 |
| OVARIAN | >−4 | >−4 | >−4 |
| RENAL | >−4 | −4.23 | −4.14 |
| PROSTATE | >−4 | −4.2 | >−4 |
| BREAST | >−4 | −4.05 | >−4 |

The most active indoles shown in Table 1, 1b and 1c, possess a high specificity for lung, melanoma, and prostate cancers. Studies described in the following section reveal that the position of the aziridinyl ring influenced neither reduction by rat liver DT-diaphorase or the percent alkylation of DNA.

When the relatively inactive indole analogues 2 are functionalized with the fused cyclopentane ring to afford cyclopent[b]indoles 3, cytotoxic activity is substantially restored in spite of the position of the aziridinyl group, Table 3

TABLE 3

Table of Log $LC_{50}$ (where $LC_{50}$ is the concentration in moles/liter causing 50% lethality) values (columns) and histological cancer type (rows) for the cyclopent[b]indole series 3b–e and 14. Each cancer type represents the average of six to eight different cancer cell lines. The lower Log $LC_{50}$ values show the increase of cytotoxicity with the addition of the fused cyclopentane ring. Melanomas are again the most sensitive cancer to this series of indoles followed by renal, colon, and non-small-cell lung cancers for the more active cyclopent[b]indole analogues 3c, 3e, and 14.

| CANCER | 3E | 3D | 3C | 3B | 14 |
|---|---|---|---|---|---|
| LEUKEMIA | >−4 | −4.06 | −4.3 | −4.06 | >−4 |
| NSC LUNG | −5.37 | −4.2 | −4.65 | −4.22 | −4.42 |
| COLON | −5.44 | −4.318 | −4.85 | −4.45 | −4.77 |
| CNS | −5.13 | −4.17 | −4.7 | −4.54 | −4.75 |
| MELANOMA | −5.99 | −4.92 | −4.99 | −4.85 | −5.06 |
| OVARIAN | −4.86 | >−4 | −4.366 | −4.05 | −4.18 |
| RENAL | −5.34 | −4.58 | −4.72 | −4.73 | −4.78 |
| PROSTATE | −4.8 | −4.46 | −4.63 | −4.5 | −4.71 |
| BREAST | −4.9 | −4.33 | −4.53 | −4.47 | −4.5 |

Studies with rat liver DT-diaphorase described below revealed that the addition of a fused cyclopentane ring to the indole system can increase the substrate specificity for this enzyme greatly. Furthermore, this fused ring increases the percent alkylation of DNA. Consequently, the addition of the fused cyclopentane ring enhance both cytotoxicity and in vivo activity. This phenomena is analogous to that seen when a fused pyrrole ring is added to the benzimidazole system. {Skibo, E. B.; Islam, I.; Heileman, M. J.; Schulz, W. G. Structure-Activity Studies of Benzimidazole—Based DNA—Cleaving Agents. Comparison of Benzimidazole, Pyrrolobenzimidazole and Tetrahydropyrido benzimidazole Analogues. *J.Med.Chem.* 1994, 37, 78–92}

In vivo Screening Results. Shown in Table 4 and FIG. 1 are B16 melanoma syngraft assays which document the in vivo activity of the cyclopent[b]indoles. Thus cyclopent[b]indoles 3c (1 and 3 mg/kg on days 1, 5, and 9 after subcutaneous implantation of $10^5$ cells in the front flank on day 0) was able to reduce the tumor mass substantially. In contrast, indole 1c decreased tumor mass only at the 3 mg/kg dose and indole 2c is inactive at both concentrations.

TABLE 4

Results of indoles 1c and 2c, and cyclopent[b]indole 3c in the B-16 melanoma model in C57/b1 mice (run at University of Arizona Cancer Center). These compounds were studied at two dose levels: 1 and 3 mg/Kg IP on days 1, 5, and 9 after tumor implantation into the front flank muscle. Shown in the table are the values for the area under the tumor-growth curve (AUC) for indoles 1c and 2c and cyclopent[b]indole 3c administered at 1 mg/kg and 3 mg/kg doses. The control was obtained with drug-free animals.

| DOSE | 1c | 2c | 3c |
|---|---|---|---|
| CONTROL | 11.39 | 11.39 | 11.39 |
| 1 mg/Kg | 10.94 | 13.83 | 6.67 |
| 3 mg/Kg | 15.82 | 8.59 | 6.92 |

Unexpectedly, the most cytotoxic compound of Table 3 (3e) was completely inactive in the B16 syngraft assays. This finding suggests that oxidative metabolism will deactivate the cyclopent[b]indole series 3. Similarly, the pyrrolo [1,2-α]benzimidazoles (PBIs) are completely noncytotoxic (50% lethal concentration or $LC_{50}>10^{-4}$ M) upon oxidation to the ketone at the 3-position, Scheme 4. However, metabolism by acyl transfer to the indole NH group to afford cyclopent[b]indole 14 will serve enhance cytotoxicity. Conversely, deacetylation reactions in the cyclopent[b]indole series will result in sustained activity.

SCHEME 4

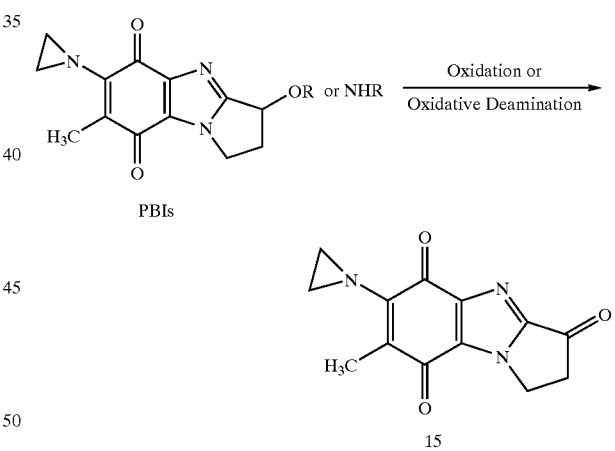

DT-Diaphorase Substrate Activity and % DNA Reductive Alkylation. Although DT-diaphorase is present in both normal and cancerous tissues this enzyme may be the key to developing selective antitumor agents. {Riley, R. J.; Workman, P. DT-diaphorase and Cancer Chemotherapy *Biochem.Pharm.* 1992, 43, 1657–1669} Depending on the organ and species source, the substrate and inhibition properties of the enzyme can vary widely. {Rauth, A. M.; Goldberg, Z.; Misra, V. DT-diaphorase: Possible roles in cancer chemotherapy and carcinogenesis. *Oncol.Res.* 1997, 9, 339–349} {Wu, K. B.; Knox, R.; Sun, X. Z.; Joseph, P.; Jaiswal, A. K.; Zhang, D.; Deng, P. S. K.; Chen, S. Catalytic properties of NAD(P)H:quinone oxidoreductase-2 (NQO2), a dihydronicotinamide riboside dependent oxidoreductase. *Arch.Biochem.Biophys.* 1997, 347, 221–228}

The structure of the enzyme even varies by ethnic origin, which may be a factor in the success of cancer chemotherapy in some patients. {Kelsey, K. T.; Ross, D.; Traver, R. D.; Christiani, D. C.; Zuo, Z. F.; Spitz, M. R.; Wang, M.; Xu, X.; Lee, B. K.; Schwartz, B. S.; Wiencke, J. K. Ethnic variation in the prevalence of a common NAD(P)H quinone oxidoreductase polymorphism and its implications for anticancer chemotherapy.*Br.J.Cancer* 1997, 76, 852–854} The differential cytotoxicity of the indole series 1 and cyclopent[b]indole series 3 discussed above could originate from differential DT-diaphorase specificity, as well as differential concentrations of this enzyme.

Figure 2:
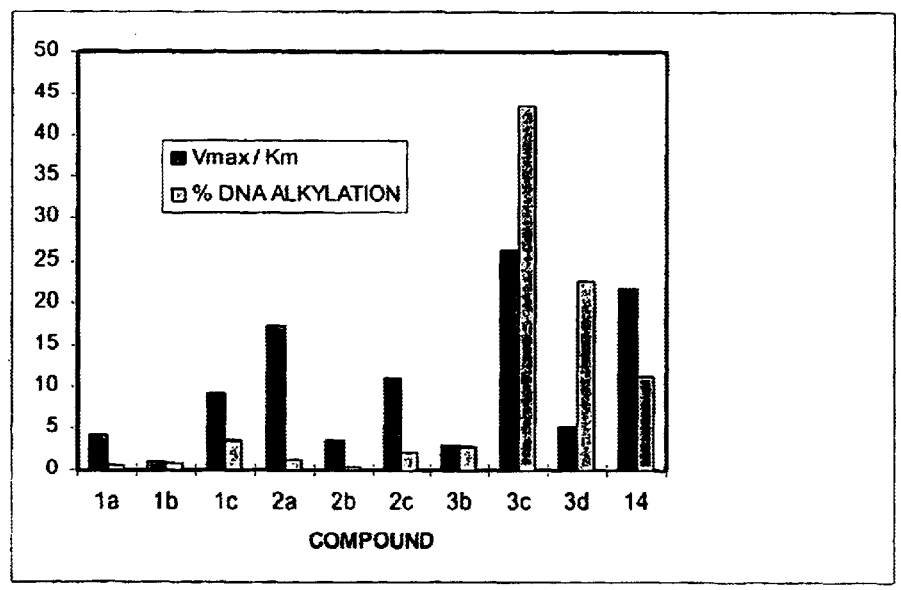
FIG. 2. Bar graph of the specificity ($V_{max}/K_m$) for rat liver DT-diaphorase and the percent DNA base pair reductive alkylation of 600 bp calf thymus DNA for the indole series 1 and 2, and cyclopent[b]indole series 3.

Next, the $V_{max}/K_M$ for reduction of the indoles with purified rat liver DT-diaphorase as well as the % reductive alkylation of 600 bp calf thymus DNA, was compared, FIG. 2. The data in FIG. 2 shows that cyclopent[b]indole 3c not only has the highest $V_{max}/K_M$ ($26.21 \times 10^{-4}$ sec$^{-1}$), but also the highest % alkylation of DNA. These observations provide a clear rationale for the observed in vivo activity of cyclopent[b]indole 3c. Likewise the active compound cyclopent[b]indole 14 is an excellent substrate for DT-diaphorase and readily alkylates DNA.

Inspection of the data in FIG. 2 reveals that the position of the aziridinyl group influences the DT-diaphorase reductase activity somewhat (compare indole 1a with indole 1a with indole 2a), but has little effect on the reductive alkylation of DNA. In fact, for the indole series 1 and 2, neither the position of the aziridinyl group nor the substituent promote DNA alkylation. For the three indole series, the acetate substituent substantially increases the specificity for DT-diaphorase compared to the hydroxyl substituent. Inspection of the components of the specificity ($V_{max}/K_M$) for the acetate-substituted indoles reveals that the acetate substituent influences the $K_M$ much like the other substituents (10–14×10$^{-4}$ M), but also provides up to a 10-fold higher $V_{max}$ value (up to 263×10$^{-9}$ M/sec).

Addition of the fused cyclopentane ring increases both the specificity for DT-diaphorase reduction, as well as the % alkylation of DNA for all analogues. Comparison of the acetate derivatives indole 2c and cyclopent[b]indole 3c reveals a large increase in substrate specificity for DT-diaphorase as well as a large increase in the % DNA alkylation.

The $V_{max}$ rather than the $K_M$ is largely responsible for this specificity difference. Addition of a fused ring, either fused pyrrole or fused cyclopentane, appears to be important for DT-diaphorase activity in some systems. Testing even showed that two fused pyrrolo rings are better than one, Chart 3. This is not a general phenomenon since reductive alkylating compounds like DZQ and EO9 do not require fused rings for activation by DT-diaphorase. {Beall, H. D.; Mulcahy, R. T.; Siegel, D.; Traver, R. D.; Gibson, N. W.; Ross, D. Metabolism of Bioreductive Antitumor Compounds by Purified Rat and Human DT-Diaphorase. *Cancer Res.* 1994, 54, 3196–3201} {Bailey, S. M.; Wyatt, M. D.; Friedlos, F.; Hartley, J. A.; Knox, R. J.; Lewis, A. D.; Workman, P. Involvement of DT-diaphorase (EC 1.6.99.2) in the DNA cross-linking and sequence selectivity of the bioreductive anti-tumour agent EO9. *Br.J.Cancer* 1997, 76, 1596–1603}

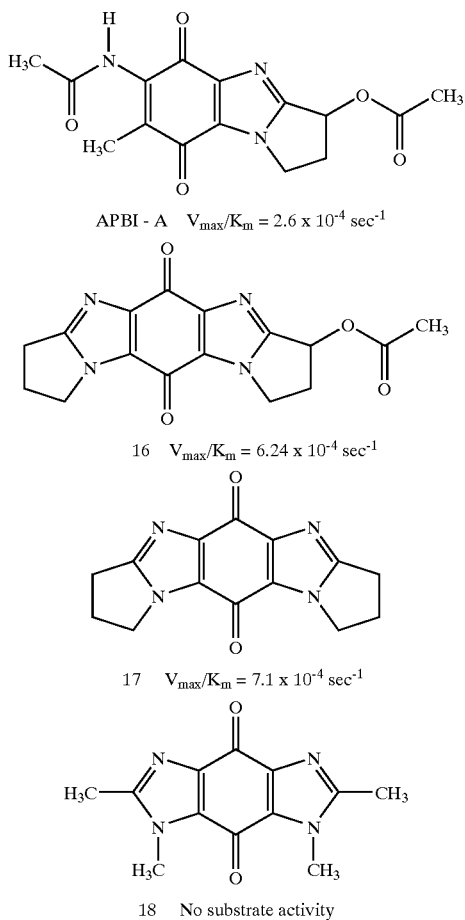

CHART 3

APBI - A  $V_{max}/K_m = 2.6 \times 10^{-4}$ sec$^{-1}$

16  $V_{max}/K_m = 6.24 \times 10^{-4}$ sec$^{-1}$

17  $V_{max}/K_m = 7.1 \times 10^{-4}$ sec$^{-1}$

18  No substrate activity

The importance of the fused ring in reductive alkylation is likely related to quinone methide formation upon elimination of acetate from the hydroquinone species, Scheme 5. Shown in this Scheme are the two possible alkylation reactions of reduced cyclopent[b]indole 3c starting with the nucleophile—mediated opening of the protonated aziridinyl group followed by quinone methide formation and nucleophile trapping of this species. The presence of the fused ring would promote elimination because the more substituted methide double bond is the product (as opposed to leaving group elimination from the methylene of reduced indoles 1c and 2c). The indole shown in the inset of Scheme 5 was prepared in this laboratory and found to be noncytotoxic in the NCI's 60 cancer cell line panel, although it could form a quinone methide species upon reduction and also was substituted with a reactive aziridinyl ring. Thus, ring fusion and the aziridinyl substituent location must be important components of cytotoxicity.

The role of ring fusion in cytotoxicity may be related to ring strain. Models shown in FIG. 3 reveal that the quinone methide derived from cyclopent[b]indole is more stable (based on a lower positive heat of formation), than that derived from the pyrrolo[1,2-α]indole. The origin of the difference in stability is the change in geometry of the indole nitrogen when the quinone methide is formed. While in the aromatic indole form, this nitrogen has sp$^2$ geometry but becomes tetrahedral when the system becomes quinonoid.

Strain results if this nitrogen is part of a five-membered ring. Thus the quinone methide derived from the cyclopent[b]indole system may form faster and have a low enough reactivity to trap nucleophiles selectively.

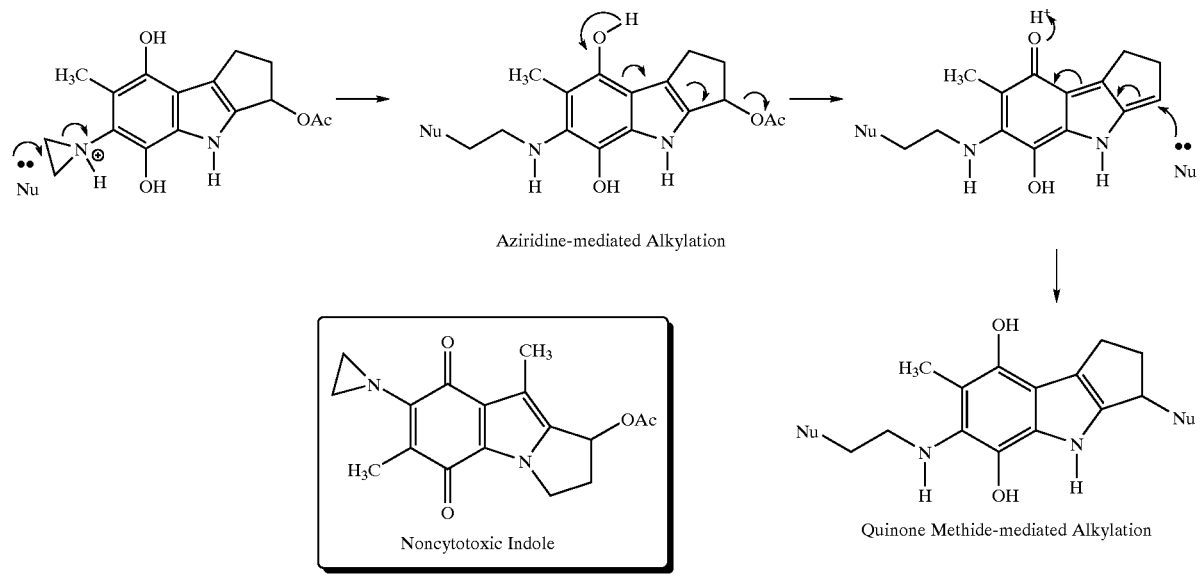

SCHEME 5

FIG. 3. Minimized structures (Austin Model I, closed shell wave function) of the cyclopent[b]indole and pyrrolo[1,2-α]indole quinone methides

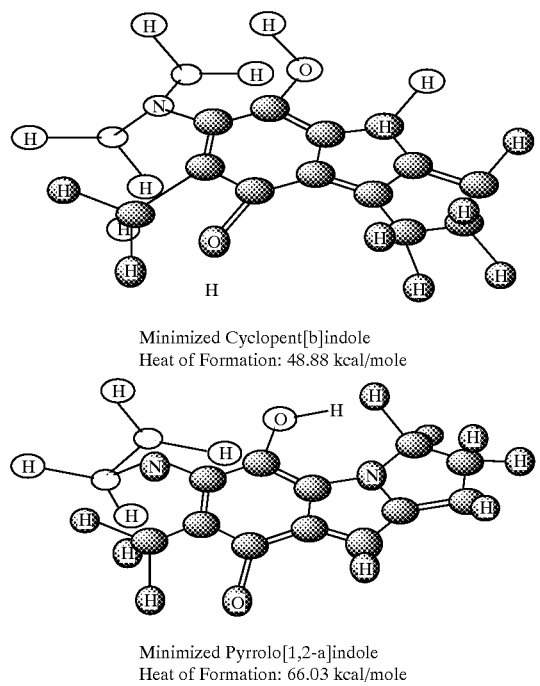

Minimized Cyclopent[b]indole
Heat of Formation: 48.88 kcal/mole

Minimized Pyrrolo[1,2-a]indole
Heat of Formation: 66.03 kcal/mole

COMPARE Analysis. COMPARE was developed at the National Cancer Institute to compare the patterns of cytotoxicity in their 60-cell line cancer panel. {Paull, D. K.; Shoemaker, R. H.; Hodes, L.; Monks, A.; Scudiero, D. A.; Rubinstein, L.; Plowman, J.; Boyd, M. R. Display and Analysis of Differential Activity of Drugs Against Human Tumor Cell Lines: Development of Mean Graph and COMPARE Algorithm. *J.Natl.Cancer Inst.* 1989, 81, 1088–1092} Antitumor agents with identical mechanisms of action possess identical or nearly identical cytotoxicity patterns (correlation coefficient>0.8). For example anthracycline analogues (doxorubicin, rubidazone, daunamycin) have a high correlation (>0.9) with each other as do the DNA alkylating agents (chlorambucil, thiotepa and triethylene melamine). The cytotoxicity ($LC_{50}$) and growth inhibition ($GI_{50}$) profiles of cyclopent[b]indole 3c were compared with those of known antitumor agents in the NCI archives. A high correlation of the $GI_{50}$ profile of cyclopent[b]indole 3c with the concentration of cellular DT-diaphorase (correlation coefficient=0.76) was observed. The cytotoxicity profile of 3c correlated well with that of mitomycin C (correlation coefficient=0.7). These correlations are consistent with the diaphorase—mediated activation and the possible DNA crosslinking reaction of reduced cyclopent[b]indole 3c.

The above show the merits of the cyclopent[b]indole ring system in the design of new DNA—directed reductive alkylating agents. The combination of cyclopent[b] fusion and the indole NH (cyclopent[b]indole 3c) results in a system exhibiting both cytotoxicity and antitumor activity. However, the addition of the N-acetyl group (cyclopent[b] indole 14) enhances antitumor activity greatly. The term cytotoxicity refers to the drug's toxicity to cancer cells in culture and the term antitumor activity refers to the drug's toxicity to cancer cells in a whole organism.

The role of the fused cyclopentane ring in cytotoxicity is as yet unclear and studies in this area continues. The cyclopent[b]indole system represents a departure from the pyrrolo[1,2-α] fusion moieties typically found in the mitomycins and mitosenes as well as the many synthetic analogues thereof such as the PBI antitumor agents developed in this laboratory. {Franck, R. W.; Tomasz, M. The Chemistry of Mitomycins; In *The Chemistry of Antitumor Agents;* Wilman, D. E., ed. Blackie & Sons, Ltd.: Glasgow, Scotland, 1990; pp 379–394} {Islam, I.; Skibo, E. B. Synthesis and Physical Studies of Azamitosene and Iminoazamitosene Reductive Alkylating Agents. Iminoquinone Hydrolytic Stability, Syn/Anti Isomerization, and Electrochemistry. *J. Org. Chem.* 1990, 55, 3195–3205}

Compound of indole series 1 and cyclopent[b]indole series 3 show a notable degree of cancer selectivity with melanoma being the common target cancer of both series. Similarly, the PBI compounds also target this type of cancer, probably because of its high DT-diaphorase concentrations. Agents in indole series 1 also target colon and prostate cancers while agents in series 3 target colon along with renal cancers and in the case of cyclopent[b]indol 3e, non-small-cell lung cancer. The mechanism of cyclopent[b]indole 3c cytotoxicity closely resembles that of mitomycin C, based on the high COMPARE correlation.

MODES FOR CARRYING OUT INVENTION

All solutions and buffers for kinetic, DNA, and electrophoresis studies used doubly distilled water. All analytically pure compounds were dried under high vacuum in a drying pistol over refluxing toluene. Elemental analyses were run at Atlantic Microlab, Inc., Norcross, Ga., FIG. 4. All TLCs (Thin Layer Chromatographs) were performed on silica gel plates using a variety of solvents and a fluorescent indicator for visualization. IR spectra were taken as thin films and the strongest absorbances reported. $^1$H NMR spectra were obtained from a 300 MHz spectrometer. All chemical shifts are reported relative to TMS.

The synthesis of new compounds are described below.

2-(Hydroxymethyl)-3,6-dimethyl-5-methoxy-4-nitroindole (5) was prepared from indole 4 by the following two step reaction.

To a mixture consisting of 500 mg (2.02 mmole) of indole 4 and 15 mL glacial acetic acid, cooled to 15° C. with a ice bath, was added 0.8 mL of nitric acid (69–71%). The reaction mixture was stirred for 15–20 min at room temperature and then poured into 100 mL of ice water and stirred for 10 min. The solids were filtered off and were washed with cold water. The wet solid was dissolved in chloroform, dried over $Na_2SO_4$ and concentrated to a residue, which was recrystallized from chloroform/hexane to afford nitrated indole 4 as yellow needles: 423 mg (70%) yield; mp:100–102° C.; TLC (chloroform/methanol, 90:10) $R_f$=0.72; IR (KBr pellet) 3447, 3319, 2926, 1676, 1529, 1282, 1207, 1155, 1026, 869, 781 cm$^{-1}$; $^1$NMR (CDCl$_3$) δ 8.76 (bs, 1H, indole), 7.29 (1H, s, H-7), 4.42 (2H, d, J=7.2 Hz, methylene of ethyl), 3.87 (3H, s, 5-methoxy), 2.44 (6H, s, 3,6-dimethyl), 1.42 (3H, t, J=7.2 Hz, methyl of ethyl); MS: [EI mode] m/z 292(M$^+$), 275 (M$^+$-OH), 263 (M$^+$-CH$_2$CH$_3$), 246, 229, 215. Anal. Calcd (C$_{14}$H$_{16}$N$_2$O$_5$) C, H, N.

To a solution of 200 mg of lithium aluminum hydride and 5 ml of dried THF, chilled to 0° C., was added 200 mg (0.68 mmol) of nitrated indole 4 in 10 mL of THF. The reaction was stirred at 0° C. for 15 min. and then slowly combined with 5 ml of ethyl acetate and stirred for 5 min. more. The solid residue was filtered off utilizing Celite and the filtrate was concentrated to dark red oil, which was dissolved in chloroform and washed with water. The chloroform was dried over $Na_2SO_4$ and concentrated to a solid residue, which was recrystallized from chloroform/hexane to afford indole 5a yellow powder: 148 mg (87%) yield; mp 152–153° C.; TLC (chloroform/methanol, 90:10)$R_f$=0.41; IR (KBr pellet) 3421, 3284, 2924, 1637, 1523, 1460, 1365, 1213, 1112, 1012, 866, 781 cm$^{-1}$; $^1$H NMR (CDCl$_3$) δ 8.33 (1H, bs, indole), 7.23 (1H, s, H-7), 4.83 (2H, d, J=5.7 Hz, 2-methylene), 3.87 (3H, s, 5-methoxy), 2.42 and 2.09 (6H, 2s, 3,6-dimethyl), 1.73 (1H, t, J=5.7 Hz, hydroxy); MS [EI mode] m/z 250 (M$^+$), 249 (M$^+$-H), 235 (M$^+$-CH$_3$) 233 (M$^+$-OH), 215, 202, 189, 174. Anal. Calcd (C$_{12}$H$_{14}$N$_2$O$_4$) C, H, N.

2,3,6-Trimethyl-5-methoxyindole-4,7-dione (6a) was prepared from indole 5 by the following two-step procedure.

A suspension of 500 mg (1.71 mmole) of indole 5 in 20 ml of methanol, containing of 250 mg of (5%) Pd on charcoal and a few drops of 2N hydrochloride acid, was shaken under 50 psi of H$_2$ for 8 h. The reaction mixture was filtered through Celite, and the filtered cake was washed with methanol. The solvent was evaporated off to afford the amine as a residue, which was used in the next step without further purification.

The residue was dissolved in a solution of 1.5 g of Fremy salt and 0.75 g of monobasic potassium phosphate in 150 mL of water. The reaction was stirred at room temperature for 4h and then extracted 3× with 50 mL of chloroform. The dried extracts (Na$_2$SO$_4$) were concentrated to an oil and then chromatographed employing silica gel with chloroform as the eluant. The product was recrystallized from chloroform/hexane to afford pure indole 6a: 92 mg (24%) yield; mp 235° C.; TLC (chloroform/methanol, 90:10)$R_f$=0.69; IR (KBr pellet) 3242, 2926, 2854, 1639, 1498, 1460, 1367, 1305, 1222, 1111, 999, 949, 763 cm$^{-1}$; $^1$H NMR (CDCl$_3$) δ 9.62 (1H, bs, indole proton), 4.00 (3H, s, 5-methoxyl) 2.25, 2.23 and 1.95 (9H, 3s, 2,3,6-trimethyl); MS (EI mode) m/z 219 (M$^+$), 204 (M$^+$-CH$_3$), 190, 176, 160, 148. Anal. Calcd (C$_{12}$H$_{13}$NO$_3$) C, H, N.

2-(Hydroxymethyl)-3,6-dimethyl-5-methoxyindole-4,7-dione (6b) was prepared from indole 5 by the following two-step procedure.

A suspension of 100 mg (0.4 mmol) of indole 5b in 15 mL of methanol, containing of 95 mg of 5% Pd on charcoal, was shaken under 50 psi of H$_2$ for 45 min. The reaction mixture was filtered through Celite, and the filtered cake was washed with methanol. The solvent was evaporated off to afford the amine as a greenish oil which was used without further purification.

The amine was dissolved in 5 ml of acetone and then combined with 5 ml of 0.055 M KH$_2$PO$_4$ buffer. This mixture was combined with a solution of 800 mg of Fremy salt in 40 mL of 0.055 M KH$_2$PO$_4$ buffer and the reaction mixture was stirred at room temperature for 45 min. The completed reaction was extracted 5× with 20 mL portions of chloroform. The dried extracts (Na$_2$SO$_4$) were concentrated to an oil and then chromatographed on silica gel with chloroform as the eluant. The product was recrystallized from chloroform/hexane to afford indole 6b as a yellow solid: 45 mg (47%) yield; mp 196–198° C.; TLC (chloroform/methanol, 90:10)$R_f$=0.43; IR(KBr Pellet) 3445, 3240, 2951, 1638, 1508, 1465, 1307, 1111, 949, 746; $^1$H NMR (CDCl$_3$) δ 9.67 (1H, bs, indole proton), 4.72 (2H, d, J=5.4 Hz, 2 methylene), 4.02 (3H, s, 5-methoxy), 2.31 (1H, t, J=5.4 Hz, hydroxy), 2.26 and 1.96 (6H, 2s, 3.6-dimethyl); MS (EI mode) m/z 235 (M$^+$), 220(M$^+$-CH$_3$), 218 (M$^+$-OH), 202, 189, 174; Anal. Calcd( C$_{12}$H$_{13}$NO$_4$)C, H, N.

5-Aziridinyl-2,3,6-trimethylindole-4,7-dione (1a). To a solution of 42 mg (0.19 mmol) of indole 6a in 8 mL of methanol was added 0.87 mL of ethyleneimine. The reaction was stirred at room temperature for 2.5 h and then the reaction mixture was placed directly on a silica gel chromatography column employing chloroform as the eluant. The product was recrystallized from chloroform/hexane to afford indole 1a as a red solid: 27 mg (60%) yield; mp 251–253° C.; TLC (chloroform/methanol, 90:10) $R_f$=0.63; IR (KBr pellet)3213, 2922, 1664, 1626, 1587, 1498, 1460, 1373, 1346, 1248, 1153, 1101, 960, 767 cm$^{-1}$; $^1$H NMR (DMSO-d$_6$) δ12.18 (1H, bs, indole proton), 2.19 (4H, s ethylene) 2.09, 2.08 and 1.89 (9H, 3s, 2,3,6-trimethyl); MS(EI mode) 230(M$^+$), 215 (M$^+$-CH$_3$), 201, 185, 174. Anal. Calcd (C$_{13}$H$_{14}$N$_2$O$_2$)C, H, N.

5-Aziridinyl-2-(hydroxymethyl)-3,6-dimethylindole-4,7-dione (1b). To a solution of 15 mg (0.06 mmole) of indole 6b in 4 mL of methanol, was added 0.35 mL (0.48 mmole) of ethylenimine. The reaction mixture was stirred at room temperature for 2.5 h and then concentrated to a residue, which was recrystallized from chloroform/hexane to afford indole 1b as a red solid: 15 mg (93%) yield; mp 224–225° C.; TLC (chloroform/methanol, 90:10) R$_f$=0.42; IR(KBr pellet) 3493, 3246, 2924, 1685, 1618, 1502, 1377, 1350, 1253, 1151, 1020,828,752 cm$^{-1}$; $^1$H NMR (CDCl$_3$) δ 9.39 (1H, bs, indole proton), 4.69 (2H, d, J=5.7 Hz, 2-methylene), 2.32 (4H, s, ethylene) 2.26 and 2.05 (6H, 2s, 3,6-dimethyl); MS (EI mode) m/z 246 (M$^+$), 229 (M$^+$-OH), 213, 201, 190, 172. Anal. Calcd (C$_{13}$H$_{14}$N$_2$O$_3$) C, H, N.

2-(Acetoxymethyl)-5-aziridinyl-3,6-dimethylindole-4,7-dione (1c). To a mixture of 10 mg of indole 1b (0.04 mmole), 5 mg (0.04 mmole) dimethylaminopyridine (DMAP) in 5 ml of chloroform, was added 100 mg of acetic anhydride. The reaction was stirred at room temperature for 25 min and then added directly to a silica gel chromatography column employing chloroform as the eluant. The purified indole 1c was recrystallized from chloroform/hexane: 11 mg (95%) yield; mp 210–212° C.; TLC (chloroform/methanol, 90:10) R$_f$=0.68; $^1$HNMR (CDCl$_3$) δ 9.38 (1H, bs, indole proton), 5.03 (2H, s, 2-methylene), 2.32 (4H, s, ethylene), 2.31 (3H, s, 3-methyl) 2.08 and 2.05 (6H, 2s, methyls); IR (KBr pellet) 3207, 2924, 1734, 1664, 1624, 1566, 1500, 1361, 1350, 1242, 1209, 1155, 1020, 962, 817, 781 cm$^{-1}$; MS (EI mode) m/z 288 (M$^+$), 245 (M$^+$-CH$_3$—C=O), 228, 213, 201, 185. Anal. Calcd (C$_{15}$H$_{16}$N$_2$O$_4$) C, H, N.

Ethyl 3,5-dimethylindole-2-carboxylate(7). To a solution of 5.6 g (0.052 mol) of p-toluidine in 15 mL of conc. HCl and 25 mL of H$_2$O, was added dropwise a solution of 3.9 g (0.057 mol) of NaNO$_2$ in 5 mL of H$_2$O at −5° C. After complete addition, the mixture was stirred at 0° C. for 15 min and brought to pH 3–4 by addition of 5 g of sodium acetate. In a separate flask, a solution of 9 g (0.055 mol) of ethyl α-ethylacetoacetate in 40 mL EtOH was cooled to 0° C. and combined with 3.5 g KOH (0.064 mol) in 10 ml H$_2$O. To this solution was added 70 g ice followed by addition of the diazonium salt prepared above. The mixture was then adjusted to pH 5–6 and stirred at 0° C. for 15 h. The completed reaction was extracted 5× with 50 mL portions of CH$_2$Cl$_2$ and the combined extracts were washed with brine and dried over Na$_2$SO$_4$. Most of the solvent was removed under reduced pressure, and the liquid residue was added dropwise to a solution of 14.5% ethanolic HCl at reflux. After refluxing this mixture for 2 h, the solvent was removed under reduced pressure and the residue was combined with a mixture of 50 mL of water and 100 mL of CH$_2$Cl$_2$. The CH$_2$Cl$_2$ layer was removed and the aqueous layer was extracted 3× with 50 mL portions of CH$_2$Cl$_2$. The combined extracts were dried over Na$_2$SO$_4$ and concentrated to a residue, which was applied to a silica gel column prepared with CH$_2$Cl$_2$. Product fractions were evaporated to afford a white solid: 5.74 g(51% )yield; mp 131–133° C.; TLC (CHCl$_3$) R$_f$=0.25; IR (KBr pellet) 3306, 2924, 2854, 1680, 1548, 1475, 1384, 1332, 1263, 798 cm$^{-1}$; $^1$HNMR (CDCl$_3$) δ 8.56 (1H, bs, indole proton), 7.43 (1H, s, 4-proton), 7.26 (1H, d, J=8.4 Hz, 7-proton), 7.15 (1H, d, J=8.4 Hz, 6-proton), 4.40 (2H, q, J=7.2 Hz, methylene) 2.59 and 2.46 (6H, 2s, 3,5-dimethyl), 1.42 (3H, t, J=7.2 Hz, methyl of ethyl); MS [EI mode] m/z 217(M$^+$), 188 (M$^+$-CH$_2$CH$_3$), 171, 142, 115. Anal. Calcd (C$_{13}$H$_{15}$NO$_2$) C, H, N.

2-(Hydroxymethyl)-3,5-dimethyl-4-nitroindole(8) was prepared from 7 by the following two-step procedure.

To a solution of 219 mg (1.01 mmol) of indole 7 in 10 mL of acetic acid, cooled in an ice/salt bath, was added dropwise a solution of 0.5 mL of nitric acid (69–71%) in 2 mL of acetic acid. After complete addition, the ice bath was removed and the reaction stirred for 4 h at room temperature. The solution was vacuum dried and purified by a silica gel flash column using CHCl$_3$ as eluant. The nitrated derivative of 7 was recrystallized from CHCl$_3$ and hexane as a yellow solid: 43.3 mg (16%) yield; mp 163–164° C.; TLC (CHCl$_3$) R$_f$=0.28; $^1$HNMR (CDCl$_3$) δ8.87 (1H, bs, indole proton), 7.40 (1H, d, J=8.4 Hz, 6-proton) 7.18 (1H, d, J=8.4 Hz, 7-proton), 4.43 (2H, q, J=7.2 Mz, methylene of ethyl), 2.47 and 2.40 (6H, s, 3,5-methyls) 1.43 (3H, t, J=7.2 Hz, methyl of ethyl); IR (KBr pellet) 3337, 2926, 1687, 1516, 1363, 1344, 1259, 1201, 1016, 775 cm$^{-1}$, MS(EI mode) 262 (M$^+$), 245 (M$^+$-OH), 216, 199, 185, 169, Anal. Calcd (C$_{13}$H$_{14}$N$_2$O$_4$)C, H, N.

The ester reduction step was the same as that employed for the preparation of 6b: 92% yield; mp 120° C.; TLC (chloroform/methanol, 90:10) R$_f$=0.30; $^1$HNMR (DMSO-d$_6$) δ 11.38 (1H, bs, indole proton), 7.42( 1H, d, J=8.1 Hz, 6-H), 7.00 (1H, d, J=8.1 Hz, 7-H), 5.25 (1H, t, J=5.7 Hz, hydroxy proton), 4.58 (2H, d, J=5.7 Hz, methylene), 2.29 (3H, s, 3-methyl) 1.98 (3H, s, 5-methyl); IR (KBr pellet) 3420, 3256, 2925, 1628, 1516, 1354, 1323, 1188, 999, 806 cm$^-$; MS (EI mode) 220 (M$^+$), 203 (M$^+$-OH), 185, 173, 156, 144, 130, 115. Anal. Calcd (C$_{11}$H$_{12}$N$_2$O$_3$)C, H, N.

2-(Hydroxymethyl)-3,5-dimethylindole-4,7-dione(9) was prepared from indole 8 by the same procedure employed for the preparation of indole 6b: 57% yield; mp 203–205° C.; TLC (chloroform/methanol, 90:10) R$_f$=0.2; $^1$H NMR (DMSO-d$_6$) δ 12.38 (1H, bs, indole proton), 6.42 (1H, q, J=1 Hz, 6-proton), 5.02 (1H, t, J=5.4 Hz, hydroxy proton), 4.38 (2H, d, J=5.4 Hz, methylene), 2.20 (3H, s, 3-methyl), 1.94 (3H, d, J=1 Hz, 5-methyl); IR (KBr pellet) 3356, 3209, 2958, 1639, 1602, 1491, 1375, 1271, 1195, 1118, 993, 889, 781 cm$^{-1}$; MS (EI mode) m/z 205 (M$^+$), 188 (M$^+$-OH), 176, 160, 148, 131, 119. Anal. Calcd (C$_{11}$H$_{11}$NO$_3$)C, H, N.

6-Aziridinyl-2-(hydroxymethyl)-3,5-dimethylindole-4,7-dione(2b) To a solution of 31.5 mg (0.15 mmol) indole 9 in 10 mL of methanol, was added 1 mL of ethyleneimine and the resulting mixture stirred at room temperature for 2 d. The solution was concentrated to dryness and the solid residue was purified by flash chromatography on silica gel using 1% methanol in chloroform as the eluant. The red product fraction was dried and recrystallized from chloroform and hexane: 8.1 mg (21%) yield; mp 227–231° C.; TLC (chloroform/methanol, 80:20) R$_f$=0.62; IR (KBr pellet) 3429, 3238, 2926, 1637, 1587, 1506, 1378, 1336, 1271, 1155, 1058, 950, 827, 748 cm$^{-1}$; $^1$H NMR (DMSO-d$_6$) δ12.21 (1H, bs, indole proton), 4.96 (1H, t, J=4.8 Hz, hydroxyl proton), 4.36 (2H, d, J=4.8 Hz, methylene), 2.20 (4H, s, ethylene), 2.17 & 1.90 (6H, 2s, 3,5-dimethyl); MS (EI mode)m/z 246 (M$^+$) ,229 (M$^+$-OH) 213, 201, 190, 172. Anal. Calcd (C$_{13}$H$_{14}$N$_2$O$_3$)C, H, N.

2-(Acetoxymethyl)-6-aziridinyl-3,5-dimethylindole-4,7-dione(2c).

To a solution of 13 mg (0.052 mmol) of indole 2b and 12 mg of 4-dimethylaminopyridine in 4 mL of dried methylene chloride was added 80 mg of acetic anhydride. The reaction mixture was stirred for 1 min and then placed directly on a silica gel column with chloroform/acetone (98:2) as the eluant. The product was recrystallized from chloroform/hexane: 13 mg (89%) yield; mp 218–220° C.; TLC (chloroform/methanol, 90:10) $R_f$=0.78; IR(KBr) 3464, 3240, 2926, 1751, 1637, 1571, 1334, 1251, 1334, 1251, 1057 cm$^{-1}$; $^1$H NMR (CDCl$_3$) δ 9.28 (1H, bs, indole NH), 5.04 (2H, s, methylene), 2.32, 2.09, 2.07(9H, 3s, methyls), 2.27(4H, s, aziridine); MS(EI mode) m/z 288(M$^+$), 245(M$^+$-CH$_3$CO), 228, 213, 201,185. Anal. Calcd(C$_{15}$H$_{16}$N$_2$O$_4$)C, H, N.

7-Methyl-1,4-dihydrocyclopent[b]indol-3(2H)-one(10). To a solution of 290 mg (1.83 mmol) of p-tolylhydrazine hydrochloride in 10 mL of ethanol was added a solution of 356 mg (3.62 mmol) of 1,2-cyclopentanedione in 10 mL of ethanol and 10 mL of conc hydrochloric acid. This mixture was refluxed at 110° C. for 3 h and then concentrated to a residue under vacuum. This residue was purified by flash chromatography on silica gel using 1% methanol in chloroform as the eluant: 55 mg (16%) yield; mp 223° C., TLC (chloroform/methanol, 95:5) $R_f$=0.50; $^1$HNMR (CDCl$_3$) δ 8.57 (1H, bs, indole proton), 7.50 (1H, s, 8-proton), 7.35 & 7.24 (2H, AB quartet, J=8.1 Hz, 5 & 6 aromatic protons), 3.07 (2H, m, 1-methylene), 2.99 (2H, m, 2-methylene) 2.46 (3H, s, 5-methyl); IR (KBr pellet) 3414, 3232, 2992, 1655, 1602, 1309, 1091, 802 cm$^{-1}$, MS(EI mode) m/z 185 (M$^+$), 170 (M$^+$-CH$_3$), 157 (M$^+$-CO), 128, 115, Anal. Calcd (C$_{12}$H$_{11}$NO) C, H, N.

1,4-Dihydro-3-hydroxy-7-methyl-8-nitro-(2H) cyclopent[b]indole (11) was prepared from cyclopent[b]indole 10 by the following two step procedure.

To a solution of 367 mg (1.98 mmol) of cyclopent[b]indole 10 in 20 mL conc sulfuric acid, was added dropwise over 15 min a solution of 199 mg (2.34 mmol) sodium nitrate in 5 mL of conc. sulfuric acid. The resulting solution was stirred for another 15 min at 0° C., and then was poured over 200 g crushed ice. The aqueous solution was extracted with 4× with 100 mL portions of chloroform. The combined extracts were washed with saturated sodium bicarbonate solution, dried over sodium sulfate, and vacuum dried. The solid residue was recrystallized from chloroform/hexane to afford the 8-nitro derivative of cyclopent[b]indole 10 as a yellow solid: 317 mg (70%) yield; mp 268° C. dec; TLC (chloroform/methanol, 95:5) $R_f$=0.62; $^1$H NMR (DMSO-d$_6$) δ 12.29 (1H, s, indole proton), 7.66 & 7.57 (1H, AB quartet, J=8.7 Hz, 5 and 6 protons), 2.98 (m, 2H, 1-methylene), 2.87 (m, 2H, 2-methylene), 2.51 (3H, s, 7-methyl); IR (KBr pellet) 3414, 3196, 2926, 1678, 1618, 1520, 1365, 1259, 1074, 835 cm$^{-1}$; MS (EI mode) m/z 230 (M$^+$) 213 (M$^+$-OH) 195, 183 (M$^+$-HNO$_2$). 171, 154, 143, Anal. Calcd (C$_{12}$H$_{10}$N$_2$O$_3$.0.2 H$_2$O) C, H, N.

To a solution of 251 mg (1.09 mmol) of the product obtained above in 40 mL of methanol was added a solution of 462 mg (12.8 mmol) of sodium borohydride in 20 mL of methanol. This solution was stirred at room temperature for 15 min followed by the addition of 50 mL of water. The aqueous solution was extracted 4× with 50 mL portions of chloroform. The extracts was dried over sodium sulfate and then vacuum dried to afford a solid residue, which was recrystallized from chloroform/hexane: 213 mg (84%) yield; mp 142–144° C.; TLC (chloroform/methanol, 90:10) $R_f$=0.50; $^1$H NMR (CDCl$_3$) δ 8.42 (1H, bs, indole proton), 7.40 & 7.04 (2H, AB quartet, J=8.1 Hz, 5- and 6-protons), 5.36(1H, m, 3-methine proton), 3.00 & 2.35 (4H, 2m, 1 & 2-methylenes protons), 2.59 (3H, s, 7-methyl); IR (KBr pellet) 3508, 3237, 2970, 1631, 1500, 1354, 1074, 804 cm$^{-1}$; MS(EI mode) m/z 232 (M$^+$), 215 (M$^+$-OH), 185 (M$^+$-HNO$_2$), 173, 156, 145. Anal. Calcd (C$_{12}$H$_{12}$N$_2$O$_3$) C, H, N.

1,4-Dihydro-3-methoxy-7-methyl-(2H) cyclopent[b]indole-5,8-dione(12) and 1,4-Dihydro-3-hydroxy-7-methyl-(2H) cyclopent[b]indole-5,8-dione(13) were both prepared from cyclopent[b]indole 11 by the following two—step procedure.

A mixture of 101 mg (0.435 mmol) of cyclopent[b]indole 11 in 40 mL methanol with 100 mg 5% Pd on carbon was reduced under 50 psi H$_2$ for 30 min. The reaction mixture was filtered through Celite and the filtrate concentrated to a residue, which was then dissolved in 5 mL of acetone. To this solution was added a solution consisting of 390 mg (2.87 mmol) of monobasic potassium phosphate and 790 mg (2.94 mmol) of Fremy salt in 80 mL of water. The resulting solution was stirred for 4.5 h and then extracted 4× with 50 mL portions of chloroform. The extracts were dried (Na$_2$SO$_4$) and then concentrated to a residue. This residue was purified by flash chromatography on silica gel using 1% methanol in chloroform as the eluant and the products were recrystallized from chloroform/hexane.

Cyclopent[b]indole 12: 16 mg (16%) yield; mp 143–145° C.; TLC (chloroform/methanol, 80:20)$R_f$=0.84; $^1$H NMR (CDCl$_3$) δ9.78 (1H, bs. indole NH), 6.41(1H, q, J=1.5 Hz, 6-proton), 4.81 (1H, m, 3-methine proton), 3.36 (3H, s, methoxy), 2.92, 2.77 and 2.42(4H, 3m, 1 & 2-methylene protons), 2.07 (3H, d, J=1.5 Hz, 7-methyl); IR (KBr pellet) 3425, 3246, 2943, 1655, 1587, 1465, 1165, 1100, 800, 669 cm$^{-1}$; MS (EI mode) m/z 231 (M$^+$), 216 (M$^+$-CH$_3$), 200 (M$^+$-OCH$_3$), 188, 174, 160, 132, 115; Anal. Calcd for (C$_{13}$H$_{13}$NO$_3$) C, H, N.

Cyclopent[b]indole 13: 20.5 mg (22%) yield; mp 199–201° C.; TLC (chloroform/methanol, 80:20)$R_f$=0.60; $^1$H NMR (CDCl$_3$) δ9.93 (1H, bs, indole NH), 6.38 (1H, q, J=1.5 Hz, 6-proton), 5.23 (1H, m, 3-methine proton), 2.92, 2.75 & 2.38 (4H, 3m, 1 & 2-methylene protons), 2.06 (3H, d, J=1.5 Hz, 7-methyl); IR (KBr pellet) 3475, 3414, 3232, 2930, 1637, 1479, 1406, 1294, 1230, 1087, 1039, 952, 912 cm$^{-1}$; MS (EI mode) m/z 217 (M$^+$), 200 (M$^+$-OH), 189 (M$^+$-CO), 174, 160, 146, 132. Anal. Calcd (C$_{12}$H$_{11}$NO$_3$) C, H, N.

6-Aziridinyl-1,4-dihydro-3-methoxy-7-methyl-(2H) cyclopent[b]indole-5,8-dione(3D) and 6-Aziridinyl-1,4-Dihydro-3-hydroxy-7-methyl-(2H) cyclopent[b]indole-5,8-dione(3b). To a solution of 0.2 mmol of cyclopent[b]indoles 12 or 13 in 20 mL of methanol was added 0.5 mL ethyleneimine and the solution was stirred at room temperature for 4 d. The solvent was removed under vacuum and the residue was purified by flash chromatography on silica gel using 5% acetone in chloroform as the eluant, and either product was recrystallized from chloroform/hexane as red prisms.

Cyclopent[b]indole 3b was obtained in 74% yield from 13; mp 193–195° C.; TLC (chloroform/methanol, 90:10)$R_f$=0.25; $^1$H NMR (CDCl$_3$) δ 9.24 (1H, bs, indole NH), 5.20 (1H, m, 3-methine proton). 3.51 (1H, d, J=4.5 Hz, hydroxy proton), 2.91, 2.73 and 2.30 (4H, 3m, 1 & 2-methylene protons) 2.29 (4H, s, aziridine), 2.07 (3H, s, 7-methyl); IR (KBr pellet). 3448, 3160, 2960, 2926, 1655, 1325, 1041, 821, 748, 601 cm$^{-1}$; MS (EI mode) m/z 258 (M$^+$), 240 (M$^+$-H$_2$O), 225 (M$^+$-H$_2$O, CH$_3$), 213, 184, 170, 158, 131; Anal.Calcd (C$_{14}$H$_{14}$N$_2$O$_3$.H$_2$O)C, H, N.

Cyclopent[b]indole 3d was obtained in 81% yield from 12; mp 186–188° C.; TLC (chloroform/methanol, 90:10)$R_f$=0.51; $^1$H NMR (CDCl$_3$) δ 9.03 (1H, bs, indole NH), 4.79 (1H, m, 3-methine proton), 3.35 (3H, s, methoxy protons), 2.90, 2.76 and 2.42 (4H, 3m, 1 & 2 -methylenes protons), 2.29 (4H, s, aziridine), 2.07 (3H, s, 7-methyl protons); IR (KBr pellet) 3277, 2924, 2859, 1655, 1643, 1591, 1340, 1097, 1026, 908, 825 cm$^{-1}$; MS (EI mode) 272 (M$^+$) 257

(M$^-$-CH$_3$), 241 (M$^+$-CH$_3$O), 225, 213, 200, 184, 172, 158, 132. Anal. Calcd For: (C$_{15}$H$_{16}$N$_2$O$_3$) C, H, N.

3-Acetoxy-6-aziridinyl-1,4-dihydro-7-methyl-(2H) cyclopent [b]indole-5,8-dione(3c) and 3-Acetoxy-4-acetyl-6-aziridinyl-1,4-Dihydro-7-methyl-(2H) cyclopent[b] indole-5,8-dione(14). To a solution of 21 mg (0.08 mmol) of cyclopent[b]indole 3b in 3 mL of methylene chloride with 22 mg 4-(dimethylamino)pyridine, was added 32 mg (0.32 mmol) acetic anhydride and the solution was stirred at room temperature for 10 min. The reaction mixture was then placed on a silica gel column employing methylene chloride as the eluent.

Cyclopent[b]indole 3c: 8.3 mg (34%) yield; mp 166–168° C.; TLC (chloroform/methanol, 90:10)R$_f$=0.68; IR (KBr pellet) 3267, 3065, 2926, 2856, 1736, 1637, 1377, 1329, 1251, 1089, 601 cm$^{-1}$; $^1$H NMR (CDCl$_3$) δ 9.26 (1H, bs, indole proton), 5.62 (1H, m, 3-methine); 2.96, 2.80 and 2.59 (4H, 3m, 1 & 2-methylene protons) 2.28 (4H, s, aziridine); 2.06 (6H, 2s, dimethyl); MS (EI mode) m/z 300 (M$^+$), 257 (M$^+$-CH$_3$CO), 240 (M$^+$-CH$_3$COOH), 225, 213, 199, 184. Anal. Calcd (C$_{16}$H$_{16}$N$_2$O$_4$.0.5 H$_2$O) C, H, N.

Cyclopent[b]indole 14: 7 mg (25%) yield; mp 135–137° C.; TLC (chloroform/methanol, 90:10)R$_f$=0.75; $^1$H NMR (CDCl$_3$) δ 6.23 (1H, m, 3-methine), 2.95, 2.84 (4H, 2m, 1 & 2 methylene), 2.73 (3H, s, 4-acetyl), 2.33 (4H, s, aziridine), 2.08 and 2.03 (6H, s, dimethyl); IR (KBr pellet) 3211, 2924, 2854, 1741, 1655, 1591, 1373, 1336, 1251, 1224, 1030, 891 cm$^{-1}$. MS (EI mode) 342 (M$^+$), 300 (M$^+$-CH$_2$CO), 283 (M$^+$-CH$_3$COO), 258, 240, 225, 213, 189, 184. Anal. Calcd (C$_{18}$H$_{18}$N$_2$O$_4$) C, H, N.

6-Aziridinyl-1,4-dihydro-7-methyl-(2H) cyclopent [b]indole-3,5,8-trione(3e). To a solution of 10.2 mg (0.04 mmol) of cyclopent[b]indole 3b in 2 mL of dried methylene chloride was added 60 mg of pyridinium dichromate. The reaction mixture was stirred at room temperature for 2 h and then flash chromatographed on a silica gel column with chloroform as the eluent. The product was recrystallized from chloroform/hexane: 2.7 mg (26% yield); IR(KBr pellet) 3257, 3159, 2928, 1699, 1637, 1577, 1518, 1340, 1255, 1147, 1051, 985 cm$^{-1}$; $^1$H NMR(CDCl$_3$) δ9.38(1H, bs, indole NH), 3.14 & 2.96(4H, 2m, 1 & 2 -methylenes), 2.33(4H, s, aziridine), 2.13 (3H, s, 7-methyl); MS(EI mode) m/z 256 (M$^+$), 241(M$^+$-CH$_3$), 227, 213, 199, 174. Anal. Calcd(C$_{14}$H$_{12}$N$_2$O$_3$) C, H, N.

6-Aziridinyl-2,3-dihydro-7-methyl-1H-pyrrolo [1.2-α] benzimidazole-3,5,8-trione(15). To a solution of 200 mg ( 0.77 mmol) of the 3-hydroxy derivative {Schulz, W. G.; Islam, E.; Skibo, E. B. Pyrrolo[1,2-α]benzimidazole-Based Quinones and Iminoquinones. The Role of the 3-Substituent on Cytotoxicity. J.Med.Chem. 1995, 38, 109–118} in 60 mL of methylene chloride was added 1 g of pyridinium dichromate and the reaction stirred for 15 h at room temperature. The solvent was then evaporated and the residue chromatographed on a silica gel column using chloroform and methanol (97:3). The dark red product band was collected, concentrated to a residue, and recrystallized from chloroform/hexane: 45 mg (23%) yield; $^1$H NMR(DMSO-d$_6$) δ 4.42and 3.2 (4H, 2t, ethylene bridge), 2.48 (4H, s, aziridinyl), 2.35 (3H, s, methyl). Anal. Calcd(C$_{13}$H$_{11}$N$_3$O$_3$) C, H, N.

Alkylation of DNA by Reduced Indoloquinones. To a mixture of 1–2 mg of sonicated (600 bp) calf thymus DNA in 2.0 mL of 0.05 M of pH 7.4 tris buffer and 2 mg of Pd on carbon was added a five-to-one base pair equivalent amount of the indoloquinone dissolved in 0.5 mL of dimethylsulfoxide. The resulting solution was degassed under argon for 30 min., after which the mixture was purged with H$_2$ for 10 min. The solution was then purged with argon for 10 min. and placed in a 30° C. bath for 24 h. The reaction was opened to the air and the catalyst was removed with a Millex-PF 0.8 μM syringe filter. The filtrate was adjusted to 0.3M acetate with a 3M stock solution of pH 5.1 acetate and then diluted with two volumes of ethanol. The mixture was chilled at −20° C. for 12 h and the DNA pellet collected by centrifuging at 12,000 g for 20 min. The pellet was redissolved in water and then precipitated and centrifuged again. The resulting blue or red pellet was suspended in ethanol, centrifuged, and dried. The dried pellet was weighed and dissolved in 1 mL of double distilled water resulting in a clear colored solution with $\lambda_{max}$~550 nm, ε~750 M$^{-1}$ cm$^{-1}$. This is the chromophore of the aminoquinone resulting from nucleophile-mediated opening of the aziridine ring. Model 2'-chloroethyl aminoquinones for extinction coefficient determination were prepared by treatment of the indoloquinone with HCl.

DT-Diaphorase Reduction Kinetics Studies. Rat liver DT-diaphorase was isolated as previously described. (H öjeberg, B.; Blomberg, K.; Stenberg, S.; Lind, C. Biospecific Adsorption of Hepatic DT-Diaphorase on Immobilized Dicoumarol.Arch.Biochem.Biophys. 1981, 207, 205–216 and Skibo, E. S.; Gordon, S.; Bess, L.; Boruah, R.; Heileman, J. Studies of Pyrrolo[1,2-α]benzimidazole Quinone DT-Diaphorase Substrate Activity, Topoisomerase II Inhibition Activity, and DNA Reductive Alkylation-J.Med.Chem. 1997, 40, 1327–1339.) Kinetic studies were carried out in 0.05 M pH 7.4 tris. HCl buffer, under anaerobic conditions, employing Thunberg cuvettes. A 2 mM stock solution of each indoloquinone was prepared in dimethyl sulfoxide (DMSO). To the top port was added the quinone stock and to the bottom port was added DT-diaphorase and NADH in the tris buffer. The top and bottom ports were purged with argon for 20 minutes and equilibrated to 30° C. The ports were then mixed and the reaction followed at 296 nm for 25 min. in order to obtain initial rates. The concentrations obtained after mixing were: 0.3 mM NADH, 1 to 20×10$^{-5}$ M quinone, and 14.5 nM (based on flavin) of enzyme active sites. The value of Δε was calculated from the initial and final absorbance values for complete quinone reduction; usual value for ε is 6000 to 8000 M$^{-1}$ cm$^{-1}$. The value of Δε was used to calculate V$_{max}$ in M sec$^{-1}$. The results were fitted to a Lineweaver-Burke plot from which V$_{max}$/K$_m$ values were calculated.

FIG. 4. Elemental Analysis:

| Compound # | (Formula) | Calculated | | | Found | | |
|---|---|---|---|---|---|---|---|
| | | C % | H % | N % | C % | H % | N % |
| Nitrated indole 4 | C$_{14}$H$_{16}$N$_2$O$_5$ | 57.5 | 5.52 | 9.59 | 57.4 | 5.52 | 9.51 |
| Indole 5 | C$_{12}$H$_{14}$N$_2$O$_4$ | 57.6 | 5.64 | 11.20 | 57.2 | 5.65 | 10.90 |
| Indole 6a | C$_{12}$H$_{13}$NO$_3$ | 65.7 | 5.98 | 6.39 | 65.9 | 6.05 | 6.37 |

-continued

| Compound # | (Formula) | Calculated C % | H % | N % | Found C % | H % | N % |
|---|---|---|---|---|---|---|---|
| Indole 6b | $C_{12}H_{13}NO_4$ | 61.3 | 5.57 | 5.95 | 61.4 | 5.62 | 6.01 |
| Indole 1a | $C_{13}H_{14}N_2O_2$ | 67.8 | 6.13 | 12.17 | 67.8 | 6.22 | 12.09 |
| Indole 1b | $C_{13}H_{14}N_2O_3$ | 63.4 | 5.73 | 11:37 | 63.5 | 5.78 | 10.85 |
| Indole 1c | $C_{15}H_{16}N_2O_4$ | 62.5 | 5.59 | 9.72 | 62.7 | 5.56 | 9.62 |
| Indole 7 | $C_{13}H_{15}NO_2$ | 71.86 | 6.96 | 6.45 | 71.82 | 6.92 | 6.41 |
| Nitrated Indole 7 | $C_{13}H_{14}N_2O_4$ | 59.53 | 5.38 | 10.68 | 59.43 | 5.36 | 10.69 |
| Indole 8 | $C_{11}H_{12}N_2O_3$ | 59.99 | 5.49 | 12.72 | 60.01 | 5.41 | 12.76 |
| Indole 9 | $C_{11}H_{11}NO_3$ | 64.4 | 5.40 | 6.83 | 64.5 | 5.42 | 6.73 |
| Indole 2b | $C_{13}H_{14}N_2O_3$ | 63.4 | 5.73 | 11.37 | 62.8 | 5.70 | 11.14 |
| Indole 2c | $C_{15}H_{16}N_2O_4$ | 62.5 | 5.59 | 9.72 | 62.6 | 5.61 | 9.54 |
| Cyclopent[b]Indole 10 | $C_{12}H_{11}NO$ | 77.81 | 5.99 | 7.56 | 77.61 | 6.02 | 7.51 |
| Nitrated Cyclopent[b]Indole 10 | $C_{12}H_{10}N_2O_3.0.2 H_2O$ | 61.5 | 4.44 | 11.96 | 61.2 | 4.54 | 11.80 |
| Cyclopent[b]Indole 11 | $C_{12}H_{12}N_2O_3$ | 62.1 | 5.21 | 12.06 | 61.8 | 5.26 | 12.03 |
| Cyclopent[b]Indole 12 | $C_{13}H_{13}NO_3$ | 67.5 | 5.67 | 6.06 | 65.9 | 5.42 | 6.21 |
| Cyclopent[b]Indole 13 | $C_{12}H_{11}NO_3$ | 66.3 | 5.10 | 6.45 | 66.3 | 5.21 | 6.41 |
| Cyclopent[b]Indole 3b | $C_{14}H_{14}N_2O_3 \cdot H_2O$ | 60.9 | 5.79 | 10.10 | 60.7 | 5.86 | 9.87 |
| Cyclopent[b]Indole 3c | $(C_{16}H_{16}N_2O_4.0.5 H_2O$ | 62.1 | 5.49 | 9.05 | 62.3 | 5.36 | 8.82 |
| Cyclopent[b]Indole 3d | $C_{15}H_{16}N_2O_3$ | 66.2 | 5.92 | 10.29 | 65.5 | 5.84 | 10.12 |
| Cyclopent[b]Indole 3e | $C_{14}H_{12}N_2O_3$ | 65.6 | 4.72 | 10.93 | 66.0 | 5.08 | 10.63 |
| Cyclopent[b]Indole 14 | $C_{18}H_{18}N_2O_4$ | 63.1 | 5.20 | 8.18 | 62.5 | 5.38 | 7.88 |
| Pyrrolo[1,2-a]benzimidazole 15 | $C_{18}H_{18}N_2O_4.0.5 H_2O$ | 58.68 | 4.54 | 15.79 | 58.43 | 4.37 | 15.46 |

Dosing.

The dosage administered will be dependent upon the identity of the neoplastic disease; the types of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of host body weight.

Expressed in terms of concentration, an active ingredient can be present in the compositions of the present invention for localized use about the cut is, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an eatable carbohydrate material, such as lactose or starch, advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies my means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oil administration such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably P.F. water, a dry powder can be formulated when insufflation is the administration of choice.

For use as aerosols, the active ingredients can be packaged in a pressurized aerosol container together with a gaseous or liquified propellant, for example, dichlorodifluoromethane, carbon dioxide, nitrogen, propane, and the like, with the usual adjuvants such as cosolvents and wetting agents, as may be necessary or desirable.

The term "unit dosage forms" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. Several dosage forms were prepared embodying the present invention. They are shown in the following examples in which the notation "active ingredient" signifies either cyclopent[b]indole 3b-e and/or indole 2a-c, and/or indole 1a-c or any other compound described herein.

Composition "A"

Hard-Gelatin Capsules

One thousand two-piece hard gelatin capsules for oral use, each capsule containing 200 mg of an active ingredient are prepared from the following types and amounts of ingredients:

| Active ingredient, micronized | 200 g |
|---|---|
| Corn Starch | 20 g |
| Talc | 20 g |
| Magnesium stearate | 2 g |

Active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 50, 250 and 500 mg amounts by substituting 50 g, 250 g and 500 g of an active ingredient for the 200 g used above.

Composition "B"

Soft Gelatin Capsules

One-piece soft gelatin capsules for oral use, each containing 200 mg of an active ingredient, finely divided by means of an air micronizer, are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

Composition "C"

Tablets

One thousand tablets, each containing 200 mg of an active ingredient are prepared from the following types and amounts of ingredients:

| Active ingredient, micronized | 200 g |
|---|---|
| Lactose | 300 g |
| Corn starch | 50 g |
| Magnesium stearate | 4 g |
| Light liquid petrolatum | 5 g |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 200 mg of the active ingredient.

The foregoing tablets are useful for treating a neoplastic disease by the oral administration of one or two tablets one to four times a day.

Using the procedure above, tablets are similarly prepared containing an active ingredient in 250 mg and 100 mg amounts by substituting 250 g and 100 g of an active ingredient for the 200 g used above.

Composition "D"

Oral Suspension

One liter of an aqueous suspension for oral use, containing in each teaspoonful (5 ml) dose, 50 mg of an active ingredient, is prepared from the following types and amounts of ingredients.

| | |
|---|---|
| Active ingredient, micronized | 10 g |
| Citric acid | 2 g |
| Benzoic acid | 1 g |
| Sucrose | 790 g |
| Tragacanth | 5 g |
| Lemon Oil | 2 g |
| Deionized water, q.s. 1000 ml | |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a neoplastic disease at a dose of 1 teaspoonful (15 ml) three times a day.

Composition "E"

Parenteral Product

The sterile aqueous suspension for parenteral injection, containing 30 mg of an active ingredient in each milliliter for treating a neoplastic disease, is prepared from the following types and amounts of ingredients:

| | |
|---|---|
| Active ingredient, micronized | 30 g |
| POLYSORBATE 80 | 5 g |
| Methylparaben | 2.5 g |
| Propylparaben | 0.17 g |
| Water for injection, q.s. 1000 ml. | |

All ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1 ml) three times a day.

Composition "F"

Suppository, Rectal and Vaginal

One thousand suppositories, each weighing 2.5 g and containing 200 mg of an active ingredient are prepared from the following types and amounts of ingredients:

| | |
|---|---|
| Active ingredient, micronized | 15 g |
| Propylene glycol | 150 g |
| Polyethylene glycol #4000, q.s. | 2,500 g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

Composition "G"

Intranasal Suspension

| | |
|---|---|
| Active ingredient, micronized | 15 g |
| POLYSORBATE 80 | 5 g |
| Methylparaben | 2.5 g |
| Propylparaben | 0.17 g |
| Deionized water, q.s. 1000 ml. | |

All ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally pharyngolaryngeally, bronchially, or orally.

Composition "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day Composition "I"

Oral Powder

One hundred grams of an active ingredient in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

Composition "J"

Insufflation

One hundred grams of an active ingredient in bulk form is finely divided by means of an air micronizer.

The foregoing composition is useful for treating antineoplastic disease, by the inhalation of 300 mg one to four times a day.

From the foregoing, it becomes readily apparent that a new and useful antineoplastic factor and new and useful antineoplastic preparations have been herein described and illustrated which fulfill all of the aforestated objectives in a remarkably unexpected fashion. It is of course understood that such modifications, alterations and adaptations as will readily occur to the artisan confronted with this disclosure are intended within the spirit of the present invention.

What is claimed is:

1. A cytotoxic and antitumour compound selected from the group consisting of: 6-Aziridinyl-1,4-Dihydro-3-hydroxy-7-methyl-(2H) cyclopent[b]indole-5,8-dione; 3-.Acetoxy-6-aziridinyl-1,4-dihydro-7-methyl-(2H) cycolpent[b]indole-5,8-dione; and 3-Acetoxy-4-acetyl-6-aziridinyl-1,4-Dihydro-7-methyl-(2H) cyclopent[b]indole-5,8-dione.

2. A compound having the structure

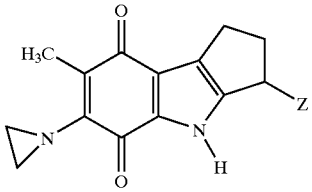

wherein: Z=—OH, —OAc, —OCH₃ or =O.

3. A compound according to claim 2 having the structure

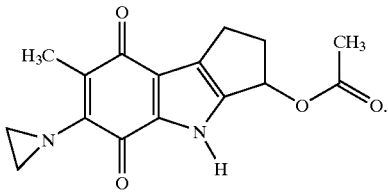

4. A method of treating humans and/or mammals afflicted with tumors and/or cancers selected from the group consisting of leukemia, lung, colon, CNS, melanoma, ovarian, renal, prostate, and breast cancers, comprising administering to said humans and/or mammals an effective amount of a compound selected from the group consisting of: 6-Aziridinyl-1,4-Dihydro-3-hydroxy-7-methyl(2H) cyclopent[b]indole-5,8-dione; 3-Acetoxy-6-aziridinyl-1,4-dihydro-7-methyl-(2H) cycolpent[b]indole-5,8-dione; and 3-Acetoxy-4-acetyl-6-aziridinyl-1,4-Dihydro-7-methyl-(2H) cyclopent[b]indole-5,8-dione.

5. A method of treating humans and/or mammals afflicted with tumors and/or cancers selected from the group consisting of leukemia, lungs, colon, CNS, melanoma, ovarian, renal, prostate, and breast cancers, comprising administering to said humans and/or mammals an effective amount of a compound having the structure

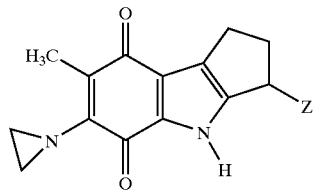

wherein Z=—OH or —OAc.

6. A method according to claim 5 comprising administering an effective amount of a compound having the structure

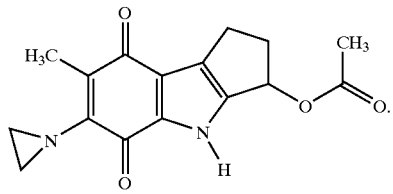

7. A composition comprising at least one of the compounds of claim 1 and a pharmaceutically acceptable carrier therefor.

8. A composition comprising at least one of the compounds of claim 2 and a pharmaceutically acceptable carrier therefor.

9. A composition comprising the compound of claim 3 and a pharmaceutically acceptable carrier therefor.

* * * * *

UNITED STATES PATENT AND TRADEMARK OFFICE
CERTIFICATE OF CORRECTION

PATENT NO. : 6,846,840 B2  
APPLICATION NO. : 10/173343  
DATED : January 25, 2005  
INVENTOR(S) : Edward B. Skibo et al.

Page 1 of 1

It is certified that error appears in the above-identified patent and that said Letters Patent is hereby corrected as shown below:

Column 1, line 14, "may own" should be changed to --has--.

Signed and Sealed this

Fifth Day of May, 2009

JOHN DOLL  
*Acting Director of the United States Patent and Trademark Office*